United States Patent [19]
Shea

[11] 3,991,210
[45] Nov. 9, 1976

[54] ACETAMIDINE URINARY ANTISEPTICS
[75] Inventor: Philip J. Shea, Midland, Mich.
[73] Assignee: The Dow Chemical Company, Midland, Mich.
[22] Filed: May 5, 1975
[21] Appl. No.: 574,787

Related U.S. Application Data
[60] Continuation-in-part of Ser. Nos. 560,268, March 20, 1975, and Ser. No. 449,813, March 11, 1974, abandoned, said Ser. No. 560,268, is a division of Ser. No. 449,813, , which is a continuation-in-part of Ser. No. 410,079, Oct. 26, 1973, abandoned, which is a continuation of Ser. No. 243,398, April 12, 1972, abandoned.

[52] U.S. Cl. ............................................... 424/326
[51] Int. Cl.² ........................................ A61K 31/155
[58] Field of Search ..................................... 424/326

[56] References Cited
OTHER PUBLICATIONS
Chemical Abstracts 65:2181–2183 (1966).

Primary Examiner—Jerome D. Goldberg
Attorney, Agent, or Firm—Maynard R. Johnson

[57] ABSTRACT
The disclosure relates to a method useful for combating microorganisms associated with infections of the urinary tract in mammals by means of administering to mammals an amount of a substituted acetamidine compound such as 2-(4-bromophenyl) acetamidine or a pharmacologically-acceptable salt thereof sufficient to provide an antiseptic amount of said compound in the urinary tract or in the urine and compositions useful in practicing the method.

15 Claims, No Drawings

ACETAMIDINE URINARY ANTISEPTICS

CROSS-REFERENCE TO RELATED APPLICATIONS

This is a continuation-in-part of my copending application Ser. No. 449,813, filled Mar. 11, 1974, which is a continuation-in-part of my application Ser. No. 410,079, filed Oct. 26, 1973, and now abandoned, which application is, in turn, a continuation of my application Ser. No. 243,298, filed Apr. 12, 1972, and now abandoned; and a continuation-in-part of my copending application Ser. No. 560,268, filed Mar. 20, 1975, which is a division of Ser. No. 449,813, filed Mar. 11, 1974, and now abandoned.

BACKGROUND OF THE INVENTION

The compounds employed in the method of the invention can be prepared as described in British Pat. No. 1,094,985; in a published Netherlands patent application by Wellcome Foundation, Ltd., Chemical Abstracts 65, 2181 (1966), and by Bell et al., J. Org. Chem. 29, 2876 (1964).

SUMMARY OF THE INVENTION

This invention is directed to a method which comprises administering to a mammal a urinary antiseptic amount of substituted acetamidine compound or a pharmacologically-acceptable salt thereof; to a composition containing such substituted acetamidine compound or salt as the active urinary antiseptic ingredient therein; and to a novel acetamidine salt; said substituted acetamidine compound corresponding to the formula:

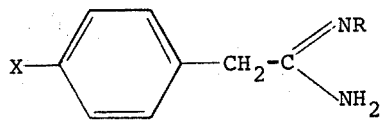

wherein X represents chloro or bromo and R represents hydrogen or hydroxyl. The method, composition and salt compound of the invention are particularly useful for combating bacterial microorganisms which may infect the mammalian urinary system. They can be employed prophylactically, to protect urinary tract organs such as the bladder, kidneys or ureter, or it may be employed therapeutically to alleviate existing infections.

It has been found that the 2-(4-halophenyl)-acetamidines, the corresponding acetamidoximes of the above formula and their pharmacologically-acceptable salts have potent urinary antiseptic properties. For the purpose of brevity, such compounds will be hereinafter referred to as "substituted amidines". Administration of one or more of the substituted amidine compounds to mammals has been found to impart valuable antimicrobial or antiseptic properties to the urine, thus providing for antimicrobial effect in the organs of the urinary tract which normally contact the urine. The compounds have little or no significant detrimental pharmacological effects at dosages consistent with good urinary antiseptic activity. The substituted amidine compounds are crystalline solids which are soluble in aqueous liquids and which in particular, are soluble in mammalian urine to an extent sufficient to provide excellent antimicrobial concentrations of the active amidine compound in the urine. In general, the pharmacologically-acceptable salts are more soluble in aqueous liquids, and the substituted amidines are preferably employed in the form of such salts.

As employed herein, the phrase "pharmacologically-acceptable salt" refers to salts of the substituted amidines, the anions of which are relatively non-toxic and innocuous to mammals at dosages consistent with good urinary antiseptic activity so that side effects ascribable to the anions do not vitiate the beneficial effects of the substituted amidines. Suitable pharmacologically-acceptable salts which can be employed in the method and composition of the invention include those derived from mineral acids such as the hydrochloride, hydrobromide, phosphate, nitrate and sulfate salts, those derived from organic carboxylic acids such as the succinate, tartrate, citrate, malate, maleate, and acetate salts and those derived from organic sulfonic acids such as the methanesulfonate and toluenesulfonate salts. particularly useful salts are the hydrochloride and p-toluenesulfonate (tosylate) salts. The novel p-toluenesulfonate salt of 2-(4-bromophenyl)acetamidine is the preferred compound of the invention.

In practicing the method, a urinary antiseptic amount of one or more substituted amidine is administered internally to a mammal by a route effective to introduce an antiseptic amount of the compound into the urinary tract of the mammal. Administration can be carried out either by a parenteral route such as by intravenous, intraperitoneal or intramuscular injection, or by introduction into the gastrointestinal tract by oral administration, for example, to introduce the compound into the urinary tract via the blood stream and the kidneys. The substituted amidines can also be introduced directly into the urinary tract by catheter, although this route is generally less desirable. An antiseptic amount of the compound appears in the urinary tract within a reasonably short period of time after oral administration, and oral administration is preferred to parenteral routes or catheterization.

In preferred procedure, a urinary antiseptic amount of the active substituted amidine or a composition containing the same is administered to a mammal having suffering from a microbial infection of the urinary tract.

The urinary antiseptic amount of compound, that is, the amount of the substituted amidine compound sufficient to provide an antiseptic or antimicrobial amount in the urinary tract depends on various factors such as the size, type and age of the animal to be treated, the particular amidine or pharmacologically-acceptable salt employed, the route and frequency of administration, the degree of infection (if any) and the organism involved, the time the compound is administered relative to prior and subsequent presentation of food and liquids; provided, however, that the animal is administered sufficient of the active substituted amidine to provide antimicrobial amount thereof in the urinary tract. In particular cases, the dosage to be administered can be ascertained by conventional range finding techniques, for example, by observing the antimicrobial activity of the urine produced at different dosage rates.

Generally, the compound is administered at dosage rates from about 0.1 to about 1 to about 4 to about 25 to about 50 to about 120 milligrams of substituted amidine compound per kilogram of animal body weight. Higher dosage rates may be employed when the compound is administered directly, as in urinary tract irrigation. When administered by intravenous injection, good results are obtained with a urinary antiseptic amount of from about 1 to about 5 or more milligrams of the amidine compound per kilogram of animal body weight. From about 3 to about 8 to about 20 to 120 milligrams of the amidine compound per kilogram, depending on dosage unit form employed, provide good results when the compound is administered orally. In the case of mammals suffering from a urinary tract infection, administration of a urinary antiseptic amount of the substituted amidine compound is preferably repeated at predetermined intervals to provide a substantially continuous antimicrobial amount of the active compound in the urinary tract until the infection is alleviated or controlled. The concentration of active compound in the urinary tract can be monitored by periodic assays of urine specimens, for example, and the state of the infection can be followed by observation of symptoms, including observation of urine. It is generally desirable to administer the individual dosages at the lowest urinary antiseptic amount which provides the desired continuity consonant with a convenient dosing schedule. In a convenient repetitive procedure, the substituted amidines are administered in single or divided oral doses at daily rates of from about 0.5 to about 8 to about 30 to 150 milligrams per kilogram per day. Daily administration, in single or divided dosages at the above rate is generally continued for from about 5 to 20 or more days. Dosage units adaptable to oral administration such as tablets, capsules, lozenges, elixirs, syrups and the like are preferred and the active amidine compound can be formulated in conventional timed release capsule or tablet formulations, in which case the preferred dosage per unit is from about 5 milligrams or less to about 10, to about 25, to about 50, to about 300 milligrams or more per unit.

Preferred compounds of the invention are those wherein X is phenyl and R is hydrogen. A particularly preferred compound is the novel compound 2-(4-bromophenyl)-acetamidine p-toluenesulfonate. This compound exhibits a high degree of urinary antiseptic activity coupled with low toxicity and physical characteristics well suited to preparation of unit dosage forms, such as tablets or capsules. In addition, this compound shows improved formulating, stability and toxicity characteristics in comparison to the corresponding hydrochloride salt. The compound can be prepared in a classical Pinner synthesis by reacting 2-(4-bromophenyl)acetonitrile with an alkanol using an acid catalyst; and reacting the resulting alkyl imidate with ammonium p-toluenesulfonate; or reacting the alkyl imidate with ammonia or a different ammonium salt, followed by hydrolysis, if necessary, and reaction with p-toluenesulfonic acid to obtain the salt.

In practicing the method of the invention, the active ingredient is preferably incorporated in a composition comprising a pharmaceutical carrier and from about 5 to about 90 percent by weight of the substituted amidine compound or a pharmacologically-acceptable salt thereof. Solid compositions, such as tablets, capsules, powders, and the like are preferred over liquid preparations such as elixirs, syrups, etc. The term "pharmaceutical carrier" refers to known pharmaceutical excipients useful in formulating pharmacologically-active compounds for internal administration to animals, and which are substantially non-toxic and non-sensitizing under conditions of use. Solid pharmaceutical carriers, such as starch, lactose, magnesium stearate, dextrose, sucrose, gelatin, microcrystalline cellulose, etc. are preferred. Suitable pharmaceutical carriers are known and disclosed in texts such as Remington's Pharmaceutical Sciences, Thirteenth Ed., Martin(Ed.), Mack Publishing Co., Easton, Pa. (1965). The compositions can be prepared by known techniques for the preparation of tablets, capsules, lozenges, troches, elixirs, syrups, emulsions, dispersions, wettable and effervescent powders, sterile injectable compositions, and can contain suitable excipients known to be useful in the preparation of the particular type of composition desired. The compositions are then administered to mammals and in particular to mammals having a urinary tract infection, particularly an infection involving *Escherichia*, *Pseudomonas* or *Proteus* microorganisms, in an amount sufficient to constitute dosage of said animal with a urinary antiseptic amount of the active amidine compound. The compounds may also be administered in conjunction with other active ingredients or other urinary antiseptic agents, for example, to utilize a combination of effects, synergistic action, combined anti-inflammatory and antiseptic activity. Combination with agents having a somewhat different spectrum of antimicrobial activity can also provide one agent having a primarily prophylactic effect while the other agent serves a primarily therapeutic effect, or it can reduce the risk of developing resistant strains of bateria, or it can be desirable merely because of the broadened antibacterial spectrum.

Particularly perferred compositions are those in unit dosage form adapted for oral administration, such as tablets and capsules, and containing from about 5 to about 10 to about 50 to about 250 milligrams of amidine compound per unit.

DESCRIPTION OF PREFERRED EMBODIMENTS

The following examples illustrate the invention but are not to be construed as limiting the same.

EXAMPLE 1

Separate groups of mice are fasted overnight, but are provided with water ad libitum prior to oral administration of a substituted amidine test compound. The test compounds are administered orally at a dosage rate of 50 milligrams of test compound per kilogram of animal body weight in an aqueous carrier. Urine is collected in sterile containers at intervals over the period from 1 to 24 hours after administration of the test compound. The collected urine is assayed for antimicrobial activity against *Escherichia coli*. *Pseudomonas aeruginosa* and a *Proteus* species, either *Proteus vulgaris* or *Proteus mirabilis*. Urine samples collected from the separate groups of mice administered one of 2-(4-chlorophenyl)acetamidine hydrochloride, 2-(4-bromophenyl)-acetamidine hydrochloride, 2-(4-chlorophenyl)acetamidoxime hydrochloride and 2-(4-bromophenyl)acetamidoxime hydrochloride are found to be active against all three test organisms. In similar operations, urine from mice administered 60 milligrams per kilogram of one of 2-(4-chlorophenoxy)acetamidine hydrochloride; 2-phenylacetamidioxime hydrochloride; and 2-(2,4-dichlorophenylacetamidoxime hydrochloride is found to be ineffective against any of the named organisms, while urine from mice administered 2-(4-nitrophenyl)acetamidoxime hydrochloride is found to be effective against E. coli, but not against the *Pseudomonas* or *Proteus* test organisms.

EXAMPLE 2

The procedure of Example 1 is repeated, employing the substituted amidine compound 2-(4-bromophenyl)-acetamidine hydrochloride, and the known antiseptics gentamicin and nalidixic acid as test compounds. Each test compound is administered in a single oral dose of 56.2 milligrams per kilogram; and separate urine samples are separately collected and assayed at intervals of 1, 4 and 24 hours after administration. The results obtained with the urine samples are set out in the following table, wherein the test organisms *E. coli*, *Pseudomonas aeruginosa* and *Proteus vulgaris* are abbreviated EC, PA and PV, and wherein the notation + indicates urinary antiseptic activity and inhibition of microbial growth being observed, and wherein O indicates that no urinary antiseptic activity and no inhibition of microbial growth are observed.

| Test Compound | Time and Organism | | | | | | | | |
|---|---|---|---|---|---|---|---|---|---|
| | 1 hour | | | 4 hours | | | 24 hours | | |
| | EC | PV | PA | EC | PV | PA | EC | PV | PA |
| 2-(4-bromophenyl)-acetamidine hydrochloride | + | + | + | + | + | + | + | O | O |
| Nalidixic acid | + | + | O | + | + | + | O | O | O |
| Gentamicin | + | + | O | O | + | O | O | O | O |

EXAMPLE 3

Separate groups of mice are separately administered an aqueous composition containing 2-(4-bromophenyl)acetamidine hydrochloride. The compound is administered per os at various dosage rates, and the animals are held for 24 hours, after which deaths are recorded, and the $LD_{50}$ (dosage lethal to 50 percent of the mice) is determined. The test compound is found to have an $LD_{50}$ of 562 milligrams per kilogram. In similar operations 2-(4-bromophenyl)acetamidine tosylate is found to have an oral $LD_{50}$ of 2610 milligrams per kilogram.

In other operations, 2-(4-bromophenyl)acetamidine hydrochloride is administered to mice at a dosage rate of 60 milligrams per kilogram in a series of standard pharmacological evaluation procedures. In such operations, the test compound is found to exhibit some antithrombotic activity and to exhibit no significant analgesic, sedative, antidepressant, anorectic, or hypotensive activity. In similar operations, 2-(4-bromophenyl)acetamidine tosylate is found to exhibit a similar pattern of activity. When the latter compound is orally administered to rats at 100 milligrams per kilogram per day, an anorectic effect is observed during the first week. This effect decreases and substantially disappears by the fourth week of dosing.

EXAMPLE 4

Several groups of Wistar rats are surgically prepared and given a urinary tract infection by injection into the lumen of the bladder of 0.1 milliliter of a brain-heart infusion broth culture of *Proteus mirabilis*, in a procedure similar to that of Miraglia, Transact. N.Y. Acad. Sc. 32, 337 (1970). One group is similarly prepared surgically, but is not infected with the test organism, providing an operated, non-infected control group. Three hours after the surgical operations are complete, the animals in three of the groups (the test groups) are orally administered 100 milligrams per kilogram of nalidixic acid, or 2-(4-bromophenyl)acetamidine hydrochloride at a dosage rate of 50 or 100 milligrams per kilogram. A fourth group is not administered any test compound to serve as an infected control group.

The animals in each group are weighed daily and the test compounds are administered to the test groups daily at the same dosage rate for a total of 14 days. At the end of the 14 day test period, the animals are sacrificed. Swabs of the kidney pelvis and samples of bladder urine are obtained and examined by bacteriological culture techniques, and pathological examinations are carried out.

In the operated, non-infected control group, weight gain and gross appearance of the kindeys, ureters and bladders is found to be normal. Cultures from swabs of the kidney pelvis and bladder urine samples are found to be bacteriologically sterile. In the operated, infected control group, cultures from swabs and bladder urine from 80 percent of the surviving rats is found to give heavy growth of the infecting *Proteus* organism. Weight gain is depressed in the animals from which the cultures are obtained, and gross pathological changes are noted in all the surviving rats in this group.

The infected rats administered 100 milligrams of nalidixic acid per kilogram per day are found to gain weight normally, and swabs from the kidney pelvis and bladder urine samples are bacteriologically sterile. No gross pathology attributable to the infection is noted.

The bacteriological examinations of the swab and urine cultures from the groups administered 2-(4-bromophenyl)acetamidine hydrochloride are found to contain no evidence of the infecting *Proteus* organism, and are bacteriologically sterile, with the exception of a slight growth of *E. coli* noted in the urine and one of the kidney swabs from one of the rats. No gross pathological changes attributable to the infection are noted in any of the rats, indicating that the *E. coli* culture is due to contamination during autopsy. The weight gain rate is found to be normal in all but one of the rats receiving 50 milligrams of substituted amidine per kilogram per day, and is normal for all the rats in this group after the tenth day of the test period. In the group administered 100 milligrams of 2-(4-bromophenyl)-acetamidine hydrochloride per kilogram, weight gain rate is found to be approximately mormal in all but two of the rats, and after the sixth day normal weight gain is observed with all but one of the test animals.

EXAMPLE 5

The operations of Example 4 are repeated using six Holtzman rats per group and using nitrofurantoin instead of nalidixic acid. The results obtained are set out in the following table.

| | Percent[1] Infection | Percent[2] Pathology | Percent Weight Gain |
|---|---|---|---|
| Operated non-infected controls | 0.0 | 0.0 | 24.2 |
| Infected controls | 100.0 | 61.8 | 15.7 |
| Nitrofurantoin, 100 mg/kg, PO | 33.0 | 13.6 | 16.9 (20.7)* |
| 2-(4-bromophenyl)acetamidine hydrochloride 50 mg/kg, PO | 60.0 | 13.6 | 16.6 |
| 2-(4-bromophenyl)acetamidine hydrochloride | | | |

-continued

|  | Percent[1] Infection | Percent[2] Pathology | Percent Weight Gain |
|---|---|---|---|
| 100 mg/kg, PO | 20.0 | 12.7 | 19.2 |

*Excluding one rat with unexplained severe weight loss.
[1]Percent of surviving rats with Proteus infection of any degree.
[2]Percent total pathology signs observed over total possible observations times 100. Pathology signs include kidney lesions, enlarged kidney, discoloration, spots or mottled kidneys, debris or calculi in bladder, hematuria or cloudy urine, enlarged or dilated ureter.

EXAMPLE 6

In a similar operation, a *Proteus mirabilis* urinary tract infection was established in rats using a similar surgical technique. In separate groups, the test compound 2-(4-bromophenyl)acetamidine p-toluene-sulfonate, or the reference compound nalidixic acid, were administered orally in three doses, 4, 28 and 52 hours after completion of the surgical technique used to establish the infection. Separate groups of rats were left untreated to serve as controls. After 72 hours, the animals were euthanized with carbon dioxide. The left kidney was removed, homogenized in 9 milliliters sterile saline solution, and fivefold dilutions of the resulting brei were made in brain-heart infusion broth. Bacterial counts in the dilutions were determined after 24 hours incubation at 37° C. The oral dose in milligrams per kilogram (mg/kg); millimoles per kilogram (mM); the number of animals in each group, and the base ten logarithm (Log$_{10}$) of the bacterial count (number of organisms per kidney) are set out below.

|  | Dose mg/kg | mM | No. of Animals | Mean Bacterial Count (Log$_{10}$) |
|---|---|---|---|---|
| Control | 0 | 0 | 38 | 7.46 |
| 2-(4-Bromophenyl)-acetamidine p--toluenesulfonate | 100 | 0.26 | 38 | 2.68 |
|  | 50 | 0.13 | 30 | 4.23 |
|  | 25 | 0.065 | 30 | 6.01 |
|  | 12.5 | 0.033 | 10 | 7.49 |
| Nalidixic Acid | 100 | 0.43 | 18 | 2.56 |
|  | 50 | 0.22 | 15 | 3.20 |

The foregoing results indicate that the amidine test compound effectively reduced bacterial counts with an effect comparable to an equal dose of nalidixic acid, on a weight basis, and that it appeared more effective, on a molar basis, than nalidixic acid in these operations.

EXAMPLE 7

980 Grams (5 moles) of 2-(4-bromophenyl)-acetonitrile, 255 grams (5.5 moles) absolute ethanol and 2500 milliliters of chloroform are mixed and cooled to about 5°–10° C. while 210 grams of hydrogen chloride gas are bubbled into the mixture over a 3 hour period. The mixture is allowed to warm to room temperature (about 25° C.) and stirred for about 48 hours. The reaction mixture is extracted with 1250 milliliters of 20 percent sodium chloride and an equal volume of ice, and the organic layer washed with 3 liters of water, then dried and concentrated under reduced pressure to a volume of about 1 liter.

The concentrate is divided into equal portions, and each portion is diluted to about 1 liter with methanol and added to 0.5 mole of ammonium p-toluene-sulfonate. The 2-(4-bromophenyl)acetamidine p-toluene-sulfonate product begins to precipitate in about 30–60 seconds after addition is complete and is collected by filtration and triturated with methanol. The product is dried and found to melt at 250°–253° C. 1230 Grams of the named product are obtained and an additional 174 grams are recovered from the filtrates by evaporation.

The product is further purified by washing with water, followed by refluxing acetone, and found to melt at 254.5°–255° C.

EXAMPLE 8

25 Parts by weight of 2-(4-bromophenyl)-acetamidine p-toluenesulfonate, 125 parts by weight of cornstarch USP, and 0.75 part by weight magnesium stearate are intimately mixed together. The mixture is filled into No. 3 hard gelatin capsules, in the amount of 150.75 milligrams per capsule. The resulting capsules, containing 25 milligrams of amidine compound per unit, are suitable for oral administration to animals in the treatment of urinary tract infections.

I claim:

1. A method for alleviating bacterial infections of the urinary tract of a mammal having such an infection, the method comprising administering internally to said mammal an effective urinary antiseptic amount of a compound corresponding to the formula:

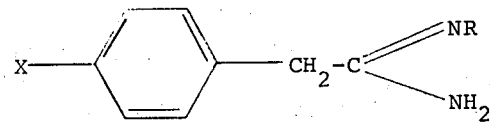

wherein X represents chloro or bromo and R represents hydrogen or hydroxyl, or a pharmacologically-acceptable salt thereof.

2. The method of claim 1 wherein R is hydrogen.
3. The method of claim 1 wherein X is bromo.
4. The method of claim 1 wherein X is chloro.
5. The method of claim 1 wherein the compound is administered orally at a dosage rate from about 1 to about 120 milligrams per kilogram of animal body weight.
6. The method of claim 5 wherein the compound is administered daily at a daily dosage rate from about 1 to about 120 milligrams per kilogram of animal body weight.
7. The method of claim 1 wherein the mammal is one having a bacterial infection of the urinary tract by a species of *Escherichia*, *Pseudomonas* or *Proteus*.
8. The method of claim 7 wherein the mammal is one having a *Proteus* infection of the urinary tract.
9. The method of claim 7 wherein the mammal is one having a *Pseudomonas* infection of the urinary tract.
10. The method of claim 1 wherein R is hydrogen and X is bromo.
11. The method of claim 10 wherein the compound is 2-(4-bromophenyl)acetamidine p-toluenesulfonate.
12. A solid composition adapted for oral administration to mammals comprising from about 5 to about 90 percent by weight of a substituted amidine compound in admixture with a solid pharmaceutical carrier; the substituted amidine compound being selected from the group consisting of a compound corresponding to the formula:

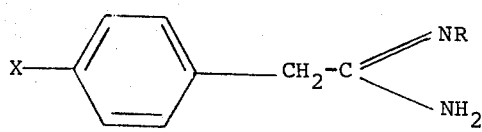

wherein X represents chloro or bromo and R represents hydrogen or hydroxyl, and a pharmacologically-acceptable salt thereof.

13. The composition of claim 12 wherein the composition is in the form of a dosage unit adapted for oral administration and containing from about 5 to about 250 milligrams of 2-(4-bromophenyl)acetamidine p-toluene-sulfonate per unit.

14. The composition of claim 12 wherein the composition is in the form of a tablet.

15. The composition of claim 12 wherein the composition is in the form of a capsule.

* * * * *